(12) United States Patent
Chandler et al.

(10) Patent No.: US 6,306,155 B1
(45) Date of Patent: Oct. 23, 2001

(54) CAPSULORHEXIS FORCEPS AND METHOD OF USE

(75) Inventors: Lamar Chandler, St. Petersburg, FL (US); Edwin G. Lee, Burlington, MA (US); Thomas Mc Linden, Woodbury; Aaron Szymanski, Bristol, both of CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/426,464

(22) Filed: Oct. 25, 1999

(51) Int. Cl.[7] .................................................. A61B 17/28
(52) U.S. Cl. ................................... 606/205; 606/170
(58) Field of Search ................................. 606/205, 206, 606/207, 208, 210, 211, 171, 170, 180, 167, 181

(56) References Cited

U.S. PATENT DOCUMENTS

| | | | |
|---|---|---|---|
| 4,706,669 | 11/1987 | Schlegel | 128/329 R |
| 4,753,235 | 6/1988 | Hasson | 128/321 |
| 4,766,897 | 8/1988 | Smirmaul | 128/305 |
| 4,785,810 | 11/1988 | Baccala et al. | 128/321 |
| 4,911,161 | 3/1990 | Schechter | 606/171 |
| 5,135,530 | 8/1992 | Lehmer | 606/107 |
| 5,167,618 | 12/1992 | Kershner | 606/22 |
| 5,269,787 | 12/1993 | Cozean, Jr. et al. | 606/107 |
| 5,275,607 | 1/1994 | Lo et al. | 606/169 |
| 5,355,871 | * 10/1994 | Hurley et al. | 606/170 |
| 5,728,117 | 3/1998 | Lash | 606/166 |
| 5,766,181 | 6/1998 | Chambers et al. | 606/107 |

OTHER PUBLICATIONS

"Closed–chamber capsulohrexis for cataract extraction combined with penetrating keratoplasty", Lee SaBaca, M.D.; Randy J. Epstein, M.D., J Cataract Retract Surg–vol. 24, May 1998, pp. 581–584, pp. 64–65 —Forceps, Asico, p. 62 —Forceps —Katena.

Akorn Ophthalmics, Utrata/Kershner Capsulorhexis Cystotome Forceps in Titanium (4 pages).

* cited by examiner

Primary Examiner—Henry J. Recla
Assistant Examiner—Vy Q. Bui
(74) Attorney, Agent, or Firm—Alan W. Fiedler

(57) ABSTRACT

A capsulorhexis forceps is described which includes a unique removable hub and handle. The hub allows the use of the forceps as a cystotome in addition to a forceps. The hub design comprises a coaxial wire inside a cannula which provides minimal trauma when the forceps is opened and closed for repositioning during the capsulotromy. The hub is also replaceable and disposable after use. This flexibility in hub replacement allows the surgeon to use the forceps either in the initial open or closed position. The handle also may provide a constant grip force to the corneal flap independent of manual actuation force of the forceps.

20 Claims, 16 Drawing Sheets

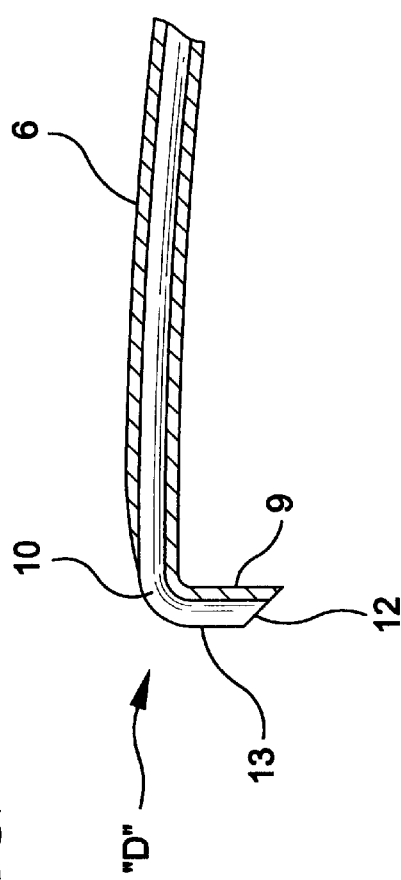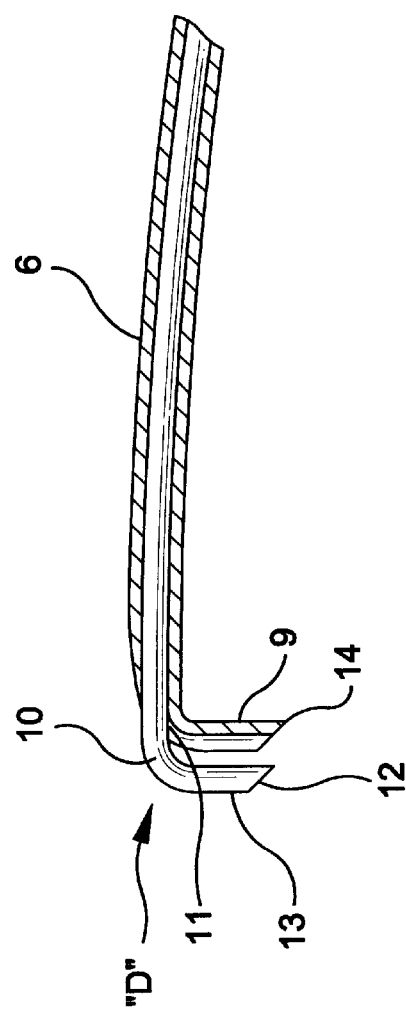

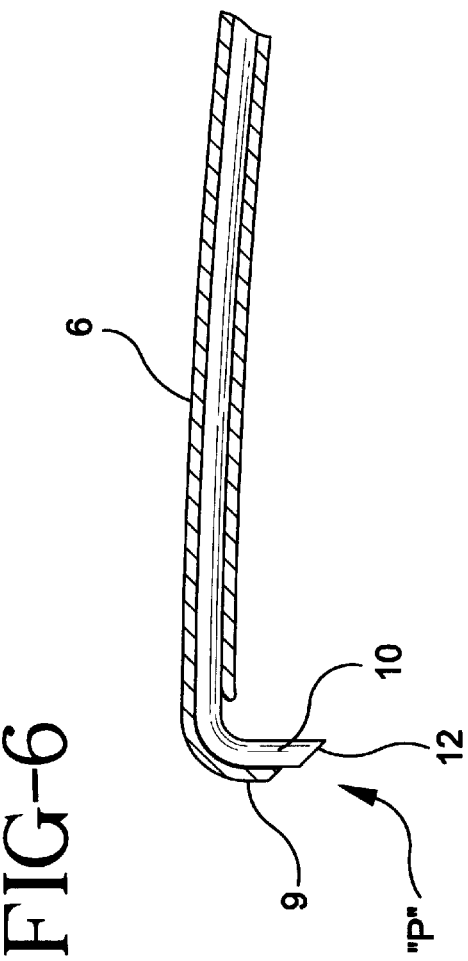
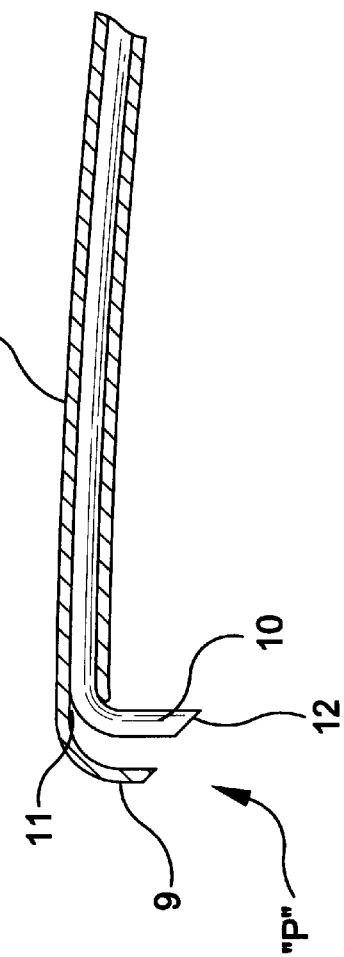

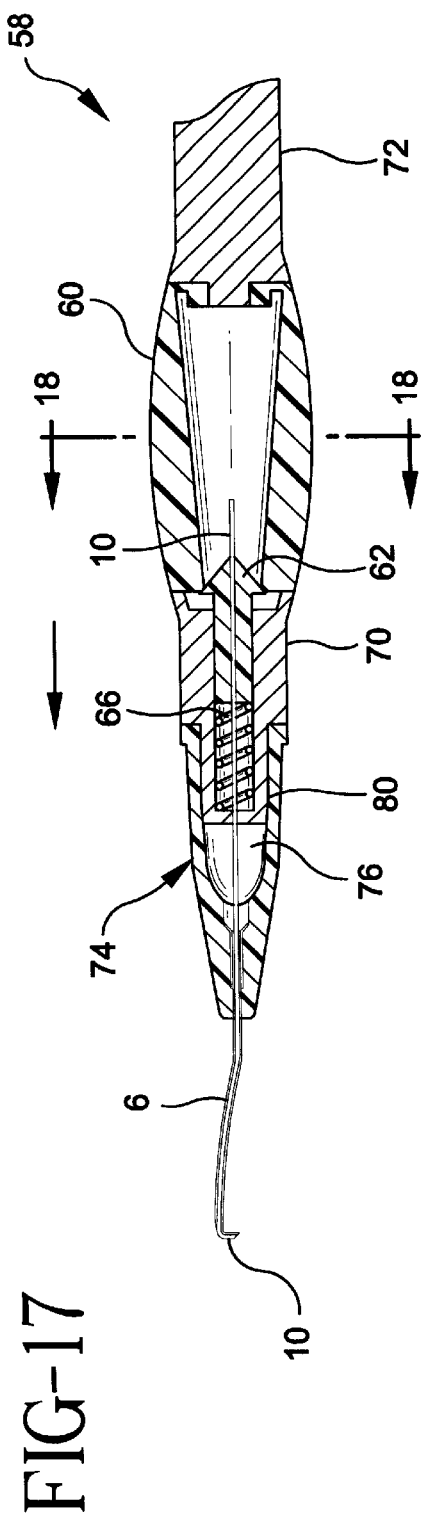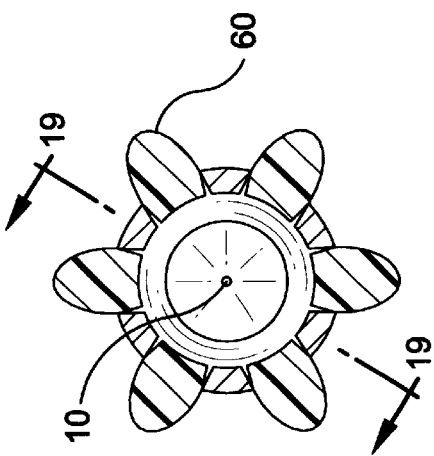
FIG-17
FIG-18

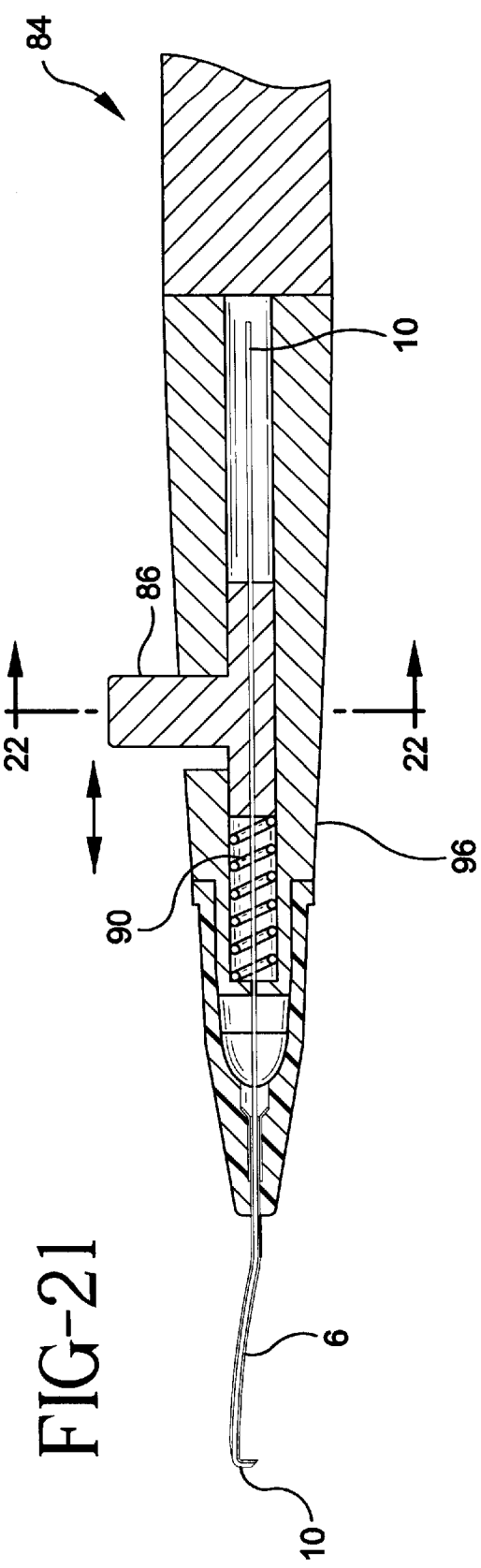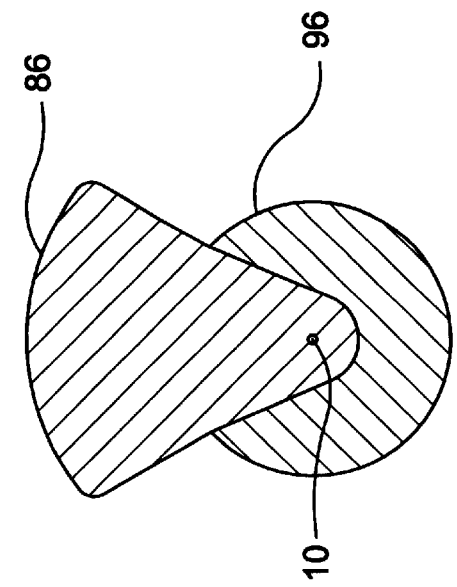

CAPSULORHEXIS FORCEPS AND METHOD OF USE

FIELD OF THE INVENTION

This invention relates to an ophthalmic surgical device. More particularly, this invention is a capsulorhexis forceps for performing continuous curvilinear capsulorhexis having a replaceable hub assembly that allows a constant grip of the cornea, and utilizes the forceps as both a forceps and a cystotome.

BACKGROUND OF THE INVENTION

In the medical visual arts, it is well known that development of cataracts, a clouding of the material within the lens capsule of the eye, is a common accompaniment to the aging process. In response to this problem, eye surgeons have developed several techniques for cataract extraction. Generally, cataract extraction involves making an incision through the anterior portion of the lens capsule. A currently known technique called a capsulotomy or more particularly a Continuous Curvilinear Capsulorhexis (hereinafter "CCC") is done to cut the anterior capsulor bag.

In this procedure, a slit incision is made in the cornea at the beginning of the continuous curvilinear capsulorhexis procedure. After the incision is made, the eye is entered with the cystotome to puncture the capsulor bag. The cystotome will either be used to continue to tear the capsulor bag or forceps will be used, after the cystotome is taken out, to make the capsulor tear. A flap is formed and is peeled off which allows the surgeon to continue with phacoemulsification procedures. At that point, direct access to the cataract lens is allowed. Clouded material is then removed through suction of the lens nucleus emulsion.

CCC is done to cut the anterior capsulor bag. One incision method done uses a cystotome or a pre-formed bent hypodermic syringe needle to enter into the anterior chamber through the pupil to access the capsulor bag. The cystotome is used to cut into the anterior portion of the capsulor bag. The problem with this technique is that there is not a lot of control with the tear of the anterior flap formed and it is not a continuous tear which produces jagged edges on the anterior portion.

Another method for performing CCC is using a cystotome in conjunction with a forceps. The cystotome is used to make a punch in the anterior capsulor bag and the forceps are used to grab the flap that was created. The anterior capsulorhexis bag is then pulled and torn by the forceps. The problems with this procedure is that there is considerable trauma to the cornea when the forceps are open and closed. Opening and closing the forceps are required to reposition the forceps to make a continuous tear in the anterior capsulor bag. By this motion, the initial incision in the eye where the forceps enters can encounter tremendous trauma.

Additionally, these two procedures are a two-step surgical procedure. There have been procedures using one device for this procedure. However, such techniques and devices can cause trauma due to stretching the incision when the forceps are opened and closed for repositioning. Such prior art techniques use one device to make the incision in the anterior capsulorhexis bag and then use it to pull and tear the flap. Such a device can be seen using the Gimbel-modified Kraff Utrata forceps. The problem with this device, like other prior art devices, is that the forceps can cause considerable trauma to the cornea when open and closed due to repositioning of the forceps when a continuous tear is required. In addition, tip damage can occur to the top of the forceps which would require replacement of the entire device. Also, the device lacks flexibility in giving the surgeon a choice of having the forceps open or closed during its initial unactuated or starting position.

Thus, there remains a need for a device that allows opening and closing of the forceps with minimal trauma to the cornea. There is also a need to provide an instrument with a replaceable tip that can cut as well as tear the anterior capsulor bag.

Other problems with current state-of the-art forceps devices for the continuous curvilinear capsulorhexis procedure is that devices can cause trauma due to variable pressure to the forceps. As the surgeon grasps the forceps, different forces on the eye may be applied due to change of grip as the anterior flap is torn. This variable in force applied to the eye could lead to trauma. There is a current need that would allow the surgeon to apply a constant grip or force to the cornea while tearing the anterior membrane. There is also a need for a device that has a replaceable tip that allows changing of the tip if the tip is damaged rather than replacing the instrument. In addition, there is a need for more flexibility in the surgical procedure to allow physicians to choose whether they would have the forceps initially opened or initially closed in the unactivated or initial starting position.

SUMMARY OF THE INVENTION

The present invention avoids the disadvantages of prior art by allowing the tip to be replaced. Replacing the tip gives the surgeon flexibility to start with an open or closed forceps. This replaceability also allows the tip to be replaced if damage to the needle occurs. The surgeon can easily replace the tip instead of discarding the instrument. A second object of this invention is that one device can be used for the surgical procedure which allows the surgeon to use a one-handed technique. This allowance could reduce the incidence of nicking interocculatory tissue. In addition, it decreases the amount of time required for this surgical procedure. Thirdly, the invention allows repositioning of the forceps without stretching the corneal tissue thus decreasing trauma to the initial incision in the eye. This device can be used in a scleral tunnel incision as well as a clear corneal incision. Lastly, the device provides constant pressure or force on the anterior membrane while gripping the anterior membrane independent of manual actuation forces.

Accordingly, there is provided in the present invention a cannula with a wire co-axially disposed within. The device performs both the incision and the forceps procedures. The cannula is attached to a replaceable hub that is attached to a handle assembly. The wire attaches to the handle assembly. The handle assembly includes at least one activation grip, a leaf spring, a shaft and a cup. Depending on whether the wire and cannula are orientated in the front or the back dictates whether the forceps are in the closed or open position initially. A spring can be disposed in the hub which allows the wire to either open or close back in its initial position. When the spring is not used in the hub, a spring in the handle is used to return the wire to its initial position. Manual gripping may be allowed by removal of the spring in the handle.

BRIEF DESCRIPTION OF THE DRAWINGS

FIG. 4 is an enlarged view of the wire in FIG. 2 co-axially within the cannula in the closed position with the front end of the wire distal to the distal end of the cannula.

FIG. 5 is an enlarged view of the wire and cannula of FIG. 4 in the open position.

FIG. 6 is an enlarged view of the wire and cannula of FIG. 3 in the closed position with the front end of the wire proximal to the distal end of the cannula.

FIG. 7 is an enlarged view of the wire and cannula in FIG. 6 in the open position.

FIG. 17 is a portion of the cross-sectional view of the alternate embodiment in FIG. 16 taken along lines 17—17.

FIG. 18 is a sectional view of FIG. 17 taken along lines 18—18.

FIG. 21 is a cross-sectional view of FIG. 20 taken along lines 21—21.

FIG. 22 is a cross-sectional view of FIG. 21 taken along lines 22—22.

DETAILED DESCRIPTION

Figure 1:
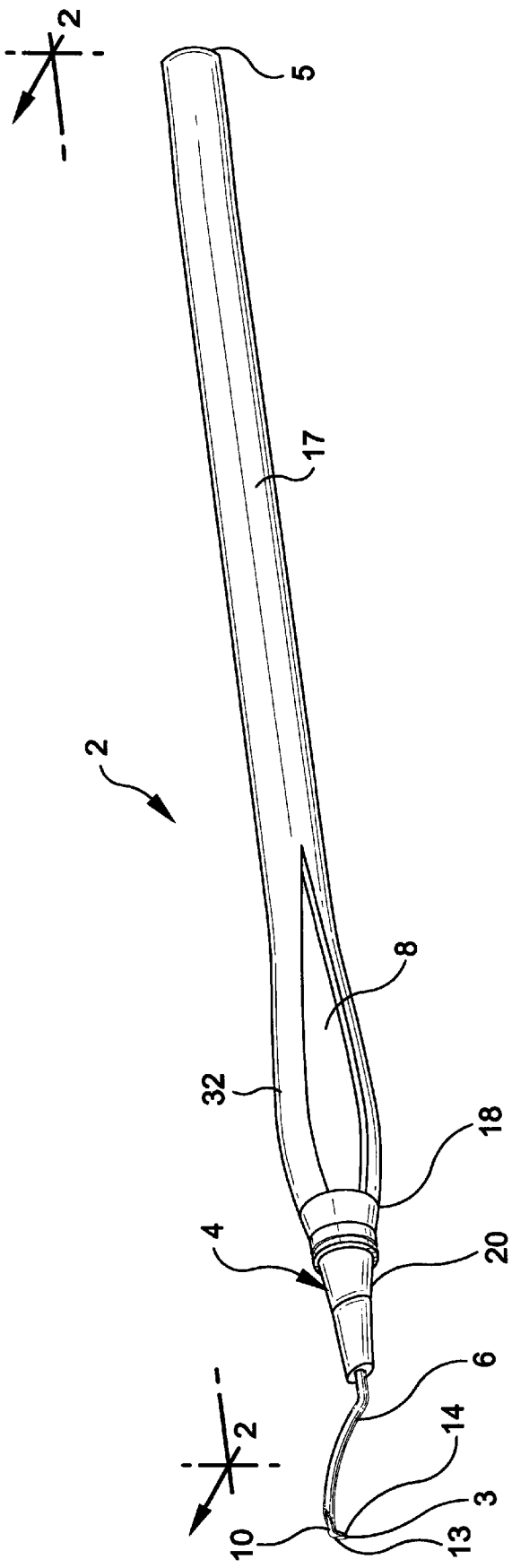
FIG. 1 is a perspective view of the capsulorhexis forceps in accordance with the subject invention.

While this invention is satisfied by embodiments in many different forms, there is shown in the drawings and herein described in detail preferred embodiments of the invention with the understanding that the present disclosure is to be considered exemplary of the principles of the invention. It is not intended to limit the scope of the invention to these embodiments illustrated. The scope of the invention will be measured by the appended claims and their equivalents.

Adverting to FIG. 1, presented is a capsulrhexis forceps 2 having a distal end 3 and a proximal end 5. The forceps also contain a disposable hub assembly 4 and a handle assembly 36. Hub assembly 4 removably locks on a distal end 18 of the handle assembly.

Disposable hub assembly 4 further includes a cannula 6, a hub 20, and a wire 10. Wire 10 is co-axially disposed inside cannula 6 such that movement of wire 10 relative to cannula 6 is available by actuation of the forceps without movement of the cannula. Cannula 6 remains preferably stationary in all embodiments of this invention.

Wire 10 can either be positioned in a proximal "P" or a distal position "D" relative to cannula 6 as shown in FIGS. 5–7. Preferably, the wire is in the distal position to allow the surgeon visual indication of the wire. By reversing the orientation of the wire relative to the cannula, the surgeon has the ability and the flexibility to choose whether the forceps are initially open or closed before actuation of the forceps. This allows more flexibility during the surgical procedure as well as easier access to the anterior capsulor bag due to the co-axial nature of the forceps. In addition, this replacement allows the surgeon to easily replace hub assembly 4 if damaged, and continue to use the same instrument. FIGS. 4 and 6 show the forceps in the closed position. FIGS. 5 and 7 show the forceps in the open position. Thus, by simply changing the hub assembly, the surgeon can change the initial position of the forceps without using a different instrument.

Preferably, the forceps are in the closed position initially, as shown in FIG. 4. When the surgeon actuates the forceps, the forceps open. Upon release of the actuation force, the forceps automatically close. This position allows the surgeon to concentrate on the peeling operation rather than concentrating on applying force to hold the flap of the anterior membrane. When the forceps are actuated, the wire moves opening the forceps as shown in FIG. 5. Release of the actuation closes the forceps on the anterior membrane. Thus, the surgeon does not have to apply force to hold the anterior membrane.

Figure 2:
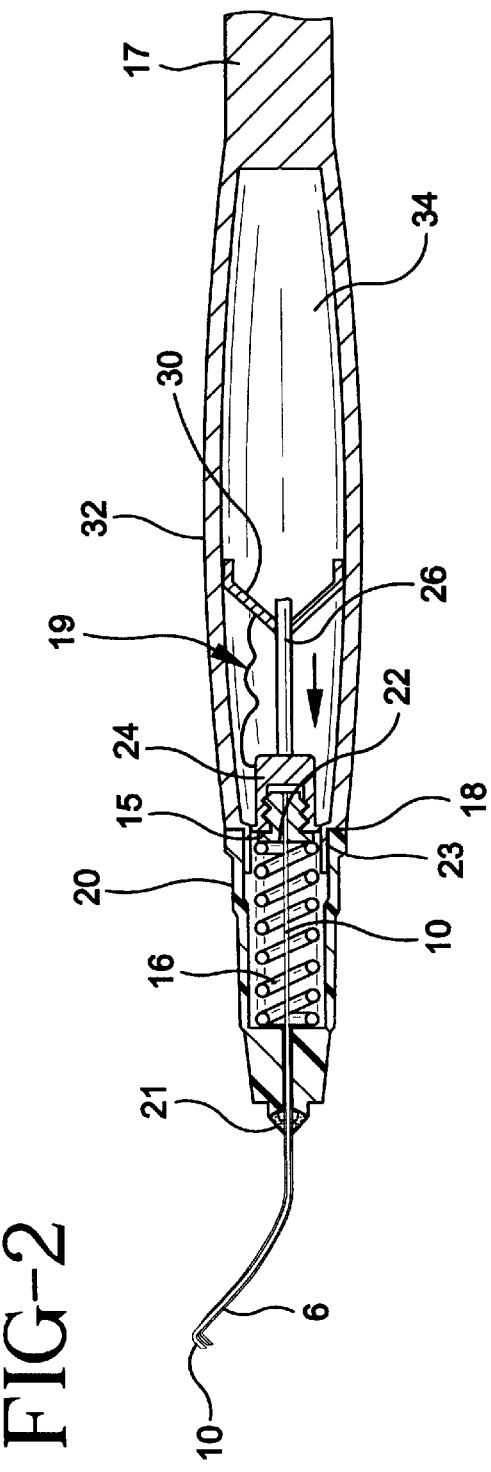
FIG. 2 is a partial cross-sectional view taken along lines 2—2 of FIG. 1.
Figure 3:
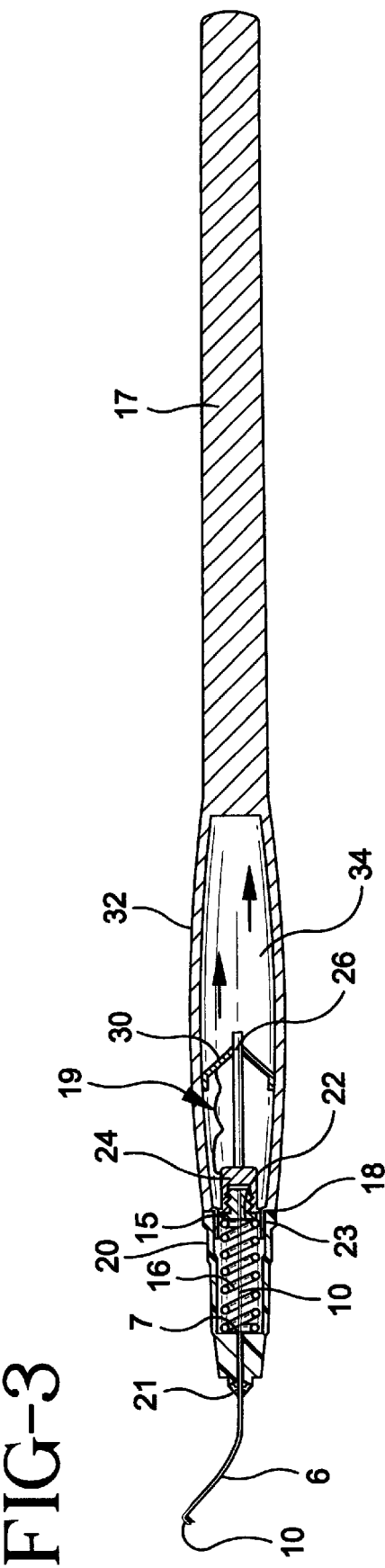
FIG. 3 is the assembly of FIG. 2 with the leaf spring in the reverse direction.

By reversing the wire's position relative to the cannula as shown in FIG. 6 and FIG. 7, initial orientation from closed to open can be realized when using the same handle assembly. By reversing the direction of motion of wire 10 as shown in FIGS. 2 and 3 by using different handle assemblies, the same hub assembly can also have two different initial orientations from open to closed. This feature gives the surgeon added flexibility in performing the capsulotomy.

Wire 10 further includes a beveled tip 12 on a front end 13. The beveled tip preferably does not have a sharp point. The wire is preferably arcuate and bent at an angle about 900 at the front end as shown in FIGS. 4–7. Cannula 6 also has a piercing tip 14 that allows puncture of the interior capsulor bag. Cannula 6 is also preferably arcuate and bent at an angle about 90° as shown in FIGS. 4–7. Cannula 6 has a piercing tip 14 which allows puncture of the interior capsulor bag. Cannula 6 also has a proximal portion 7, a distal portion 9 and a lumen 11. Preferably proximal portion 7 is attached to hub 20.

Hub assembly 4 also includes a hub 20 which preferably contains a spring 16 therein. However, as will later be shown, spring 16 need not be in hub 20 for forceps 2 to function. As shown in FIGS. 2 and 3, spring 16 is attached to a cap 22 to provide tension to wire 10D. Spring 16 need not be attached to cap 22 so long as there is contact between the spring and the cap. Wire 10 is preferably attached to cap 22. There are many methods known by those also skilled in the art for attaching wire 10 to cap 22 and spring 16 to cap 22. Such methods include but are not limited to sonic welding, snap fits, heat welding, fasteners, insert molding and adhesives. The function of spring 16 is to return wire 10 back to its initial position after the wire moves by actuation of the forceps. Wire 10 has also a front end 13 and a back end 15. Preferably, the wire is attached at the back end to the cap.

Capsular forceps 2 further include handle assembly 36. Preferably, handle assembly 36 includes at least one activation grip 32, a handle 17 and a wire actuation system 19. Adjacent to a distal end 18 of the handle, is located the grip.

This positioning allows ease of use. Activation grips 32 are used to activate the forceps, and move the wire. Attached to activation grips 32 is a leaf spring 30. Leaf spring 30 can be attached to the activation grips by many methods known by those skilled in the art. It is within the scope of the invention to include leaving out the spring leaf from actuation system 19. This would allow the surgeon to use the forceps like a conventional forceps where the forceps do not automatically open and close. Preferably, the leaf spring is present and attached to a central shaft 26. Central shaft 26 comprises a cup 24 adjacent to distal end 18. Preferably, wire actuation system 19 includes the leaf spring, central shaft and cup. However, as will be detailed in other embodiments, these elements can be changed or eliminated as previously described for the leaf spring. Cup 24 is attached to cap 22. Cap 22 attaches to cup 24 when disposable hub assembly 4 is attached to handle assembly 36. There are many methods for the cap to be inserted into the cup. Such mechanisms and methods include threads, snap fits, slip fits, luer locks and other such removably connected fixtures.

Hub assembly 4 is connected to handle assembly 36 by a slip fit or luer lock fit at the distal end of handle assembly 36. Preferably, handle assembly 36 provides a mechanism for easily removing the hub assembly and securely mounting the hub assembly during the surgical procedure. Preferably, hub assembly 4 is pre-packaged separately from the handle assembly. During the surgical procedure, the surgeon can remove the hub assembly from the package and attach it to the handle assembly.

The capsulorhexis forceps 2 is closed initially in the pre-packaged state. When assembled to the handle assembly, the wire relative to the cannula can be in either the closed position or open position depending on the position of leaf spring 30. When the activation grips are depressed, as shown in FIGS. 2 and 3, leaf spring 30 is depressed moving the central shaft. Central shaft 26 moves in the distal or proximal direction, depending on the position of the leaf spring, forcing cup 24 and attached cap 22 also in the related direction. This movement compresses spring 16 and forces wire 10 in a distal direction to open the forceps, as shown in FIG. 2. FIG. 3 shows spring 16 in tension and forces wire 10 in a proximal direction to close the forceps. As previously noted, by changing the proximal and distal positioning of wire 10 and cannula 6, the forceps can be altered from an initially closed position to an initially open position or vice versa.

By reversing the position of leaf spring 30 or the handle assembly as shown in FIG. 3, depressing activation grips 32 moves central shaft 26 in a proximal direction. This allows a hub assembly with wire 10 and cannula 6 initially in the open position to close by forcing cup 24 and cap 22 in the proximal direction. Thus, wire 10 is pulled in the proximal direction and spring 16 is put into tension. Upon releasing activation grips 32, spring 16 recompresses thereby putting wire 10 back in its initial open position.

The above embodiment can also provide for both initial open and initially closed positions with the leaf spring in a constant position merely by changing the orientation of wire 10 relative to cannula 6 as shown in FIGS. 4–7. By reversing the position of wire 10 as shown in FIG. 6–7 which has wire 10 behind cannula 6, FIG. 2 can initially be opened rather than initially closed. Thus, depressing activation grips 32 allows wire 10 to be moved in the distal direction and thereby closing the forceps. In a similar situation, FIG. 3 using a hub assembly with reversed position of the cannula and the wire as shown in FIGS. 6 and 7 would allow the forceps to initially be in the closed position when attached and when the activation grips are depressed would allow the forceps to open.

However, it is preferred that wire 10 be on the outside or distal position relative to cannula 6. This position is preferred because it allows the surgeon visual indication and positioning of the wire. In addition, it is preferred that the forceps are in the closed position initially thus providing the surgeon with the advantage of having less trauma to the eye since the surgeon does not have to concentrate on holding the flap of the anterior membrane. Handle assembly 36, when it includes the leaf spring or the spring in the hub, provides a constant force to the corneal or anterior membrane regardless of the manual force exerted by the surgeon on the grips. This is due to the wire actuation system and, also when present, the spring located in the hub. The present invention allows the greatest flexibility to the surgeon by having the replaceable hub that allow the forceps to be either in the closed or open position before actuation. In addition, if the wire or the cannula is damaged, only the hub assembly need be replaced not the entire forceps.

By preferably having wire 10 co-axially inside cannula 6, trauma to the eye may be reduced when the forceps is opened and closed due to re-positioning. This feature is due to the wire moving linearly with respect to the cannula during opening and closing of the forceps. Additionally, since the forceps also acts as a cystotome by having a piecing tip 14 on the cannula 6, one device is used instead of two for this procedure. Using one device for this procedure allows the surgeon to use a one-handed technique that may further reduce the incidence of accidental trauma to the eye.

Wire actuation system 19 in FIG. 2 and FIG. 3 is in a cavity 34 inside handle 17. An opening 8 as shown in FIG. 1 can be used to give the actuation grip the flexibility needed to move. Actuation grips 32 are preferably made of a flexible material. Such material would include thermoplastic elastomers, natural rubber and flexible metals such as aluminum.

Hub 20 further includes a first end 21 and a second end 23. Second end 23 removably attaches to distal end 18. When the hub is attached to the handle assembly, cap 22 removably attaches into cup 24.

Figure 8:
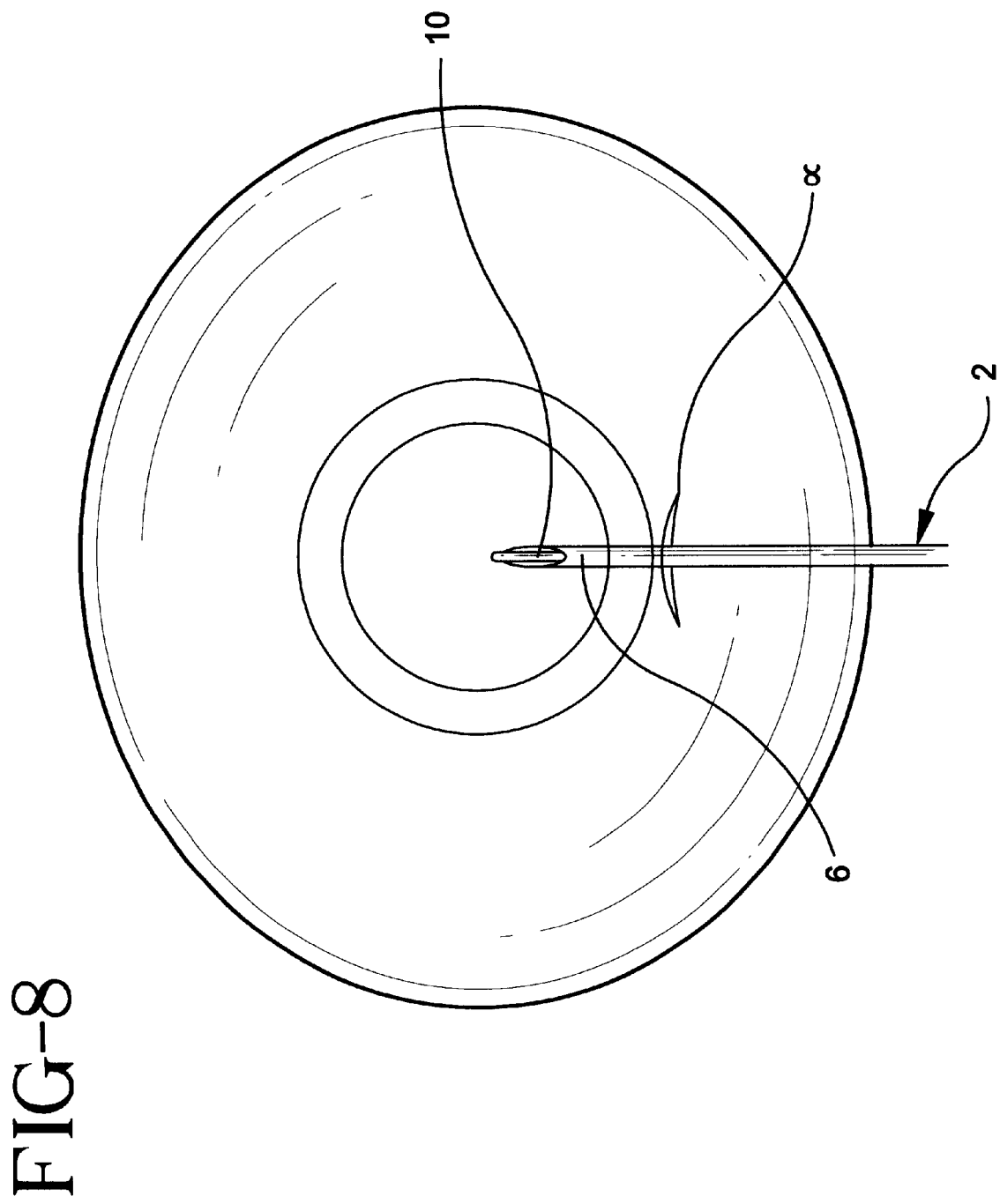
FIG. 8 is a top view of the subject invention entering the anterior capsulor bag.
Figure 9:
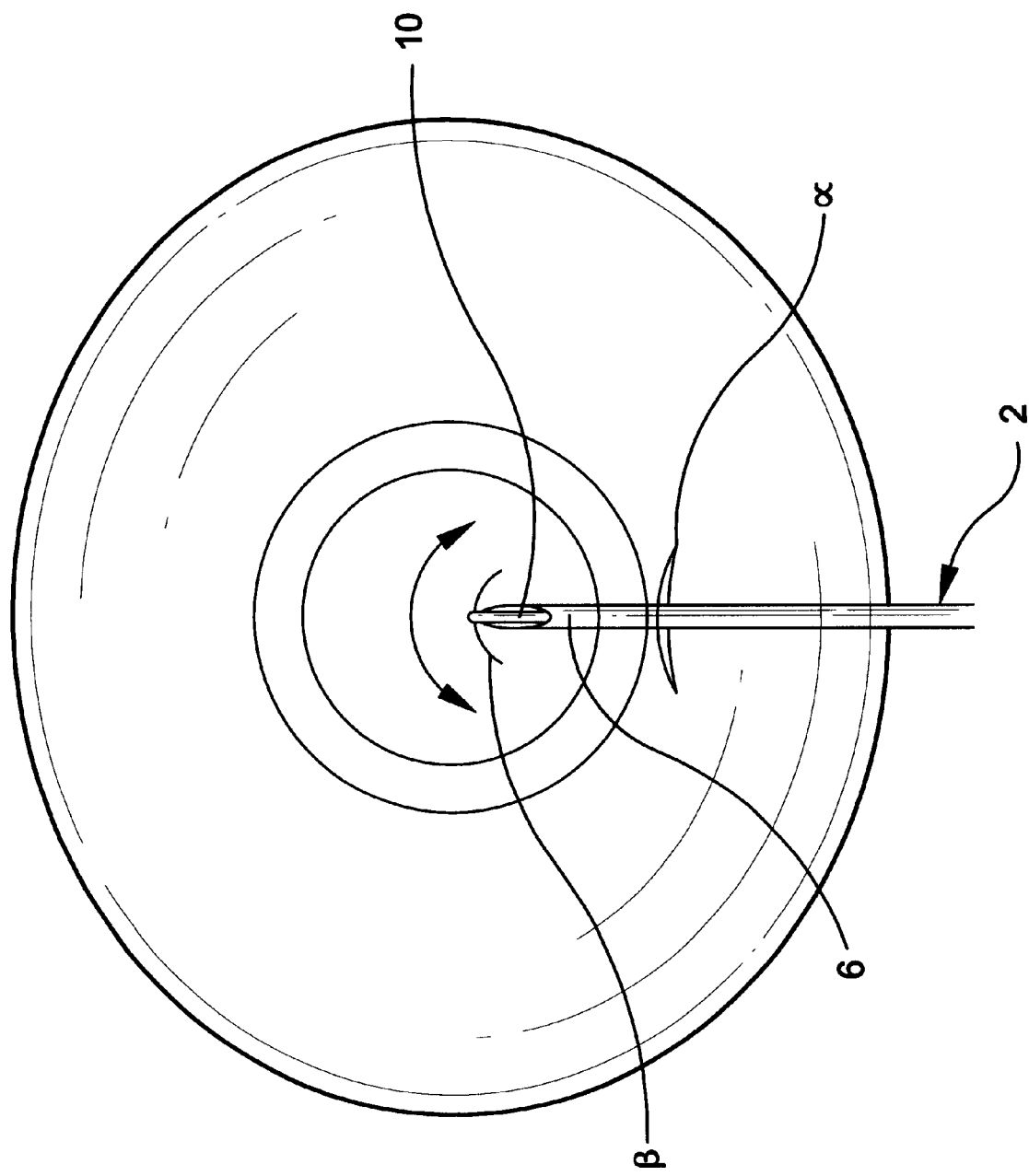
FIG. 9 is a top view of the subject invention cutting the anterior capsulorhexis bag.
Figure 10:
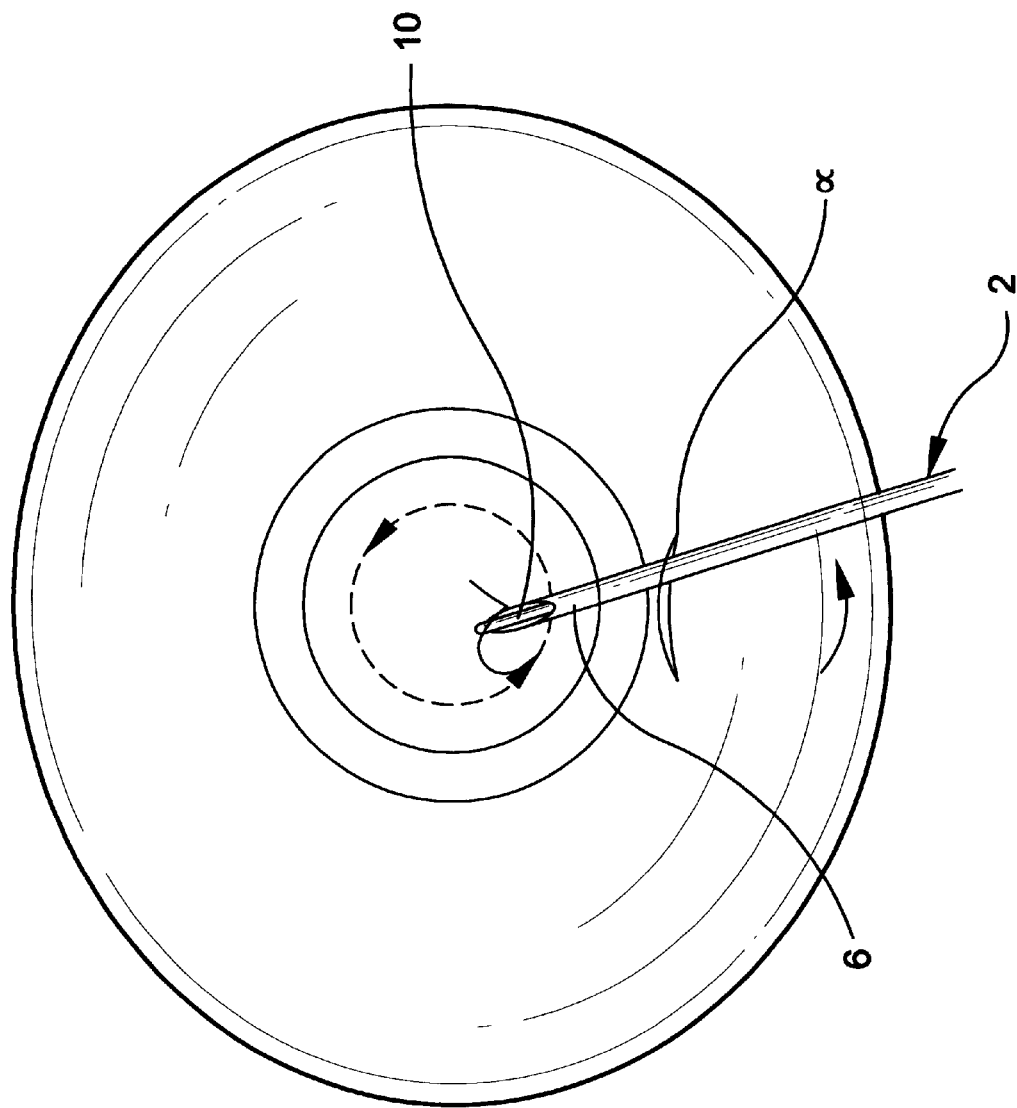
FIG. 10 is a top view of the subject invention tearing and peeling the anterior capsulorhexis bag.
Figure 11:
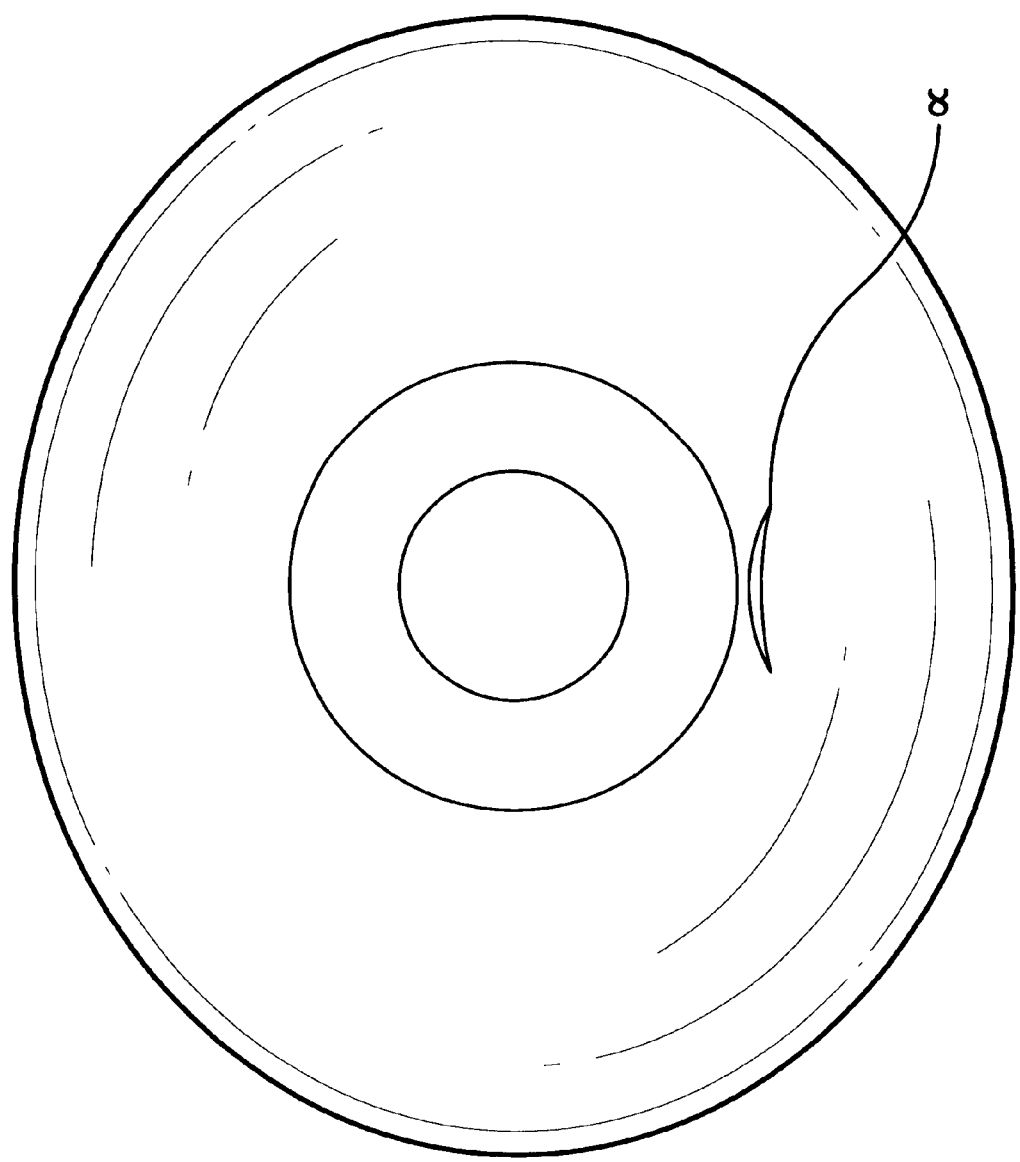
FIG. 11 is the view in FIG. 10 with the anterior capsulorhexis flap removed.
Figure 12:
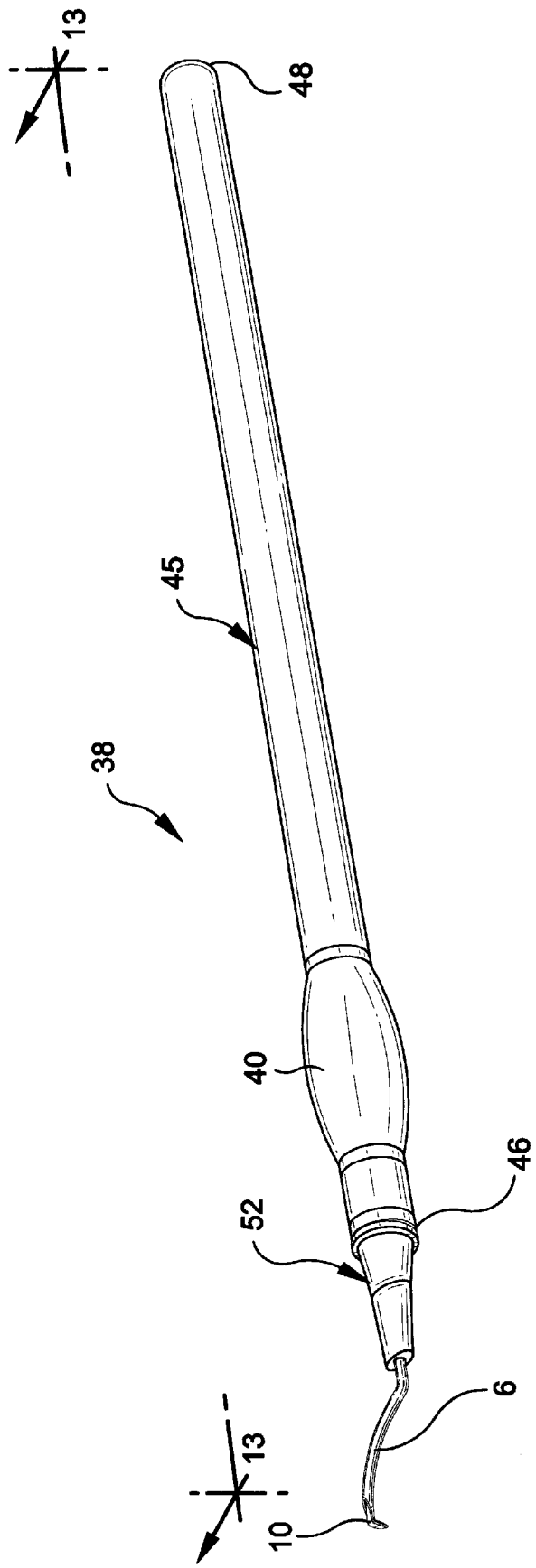
FIG. 12 is a perspective view of an alternate embodiment.

Adverting to FIG. 8, shown is the capsulorhexis forceps of the present invention inserted into the anterior capsulor bag. Forceps 2 is inserted into a primary incision "α". The incision can either be pit in the scleral tunnel or the clear corneal positions. FIG. 8 illustrates an incision in the scleral tunnel position. For CCC procedures, scleral tunnel incisions are preferred. In FIG. 9, the capsulorhexis forceps makes a second incision "β" on the anterior capsulor bag using the same capsulorhexis forceps. Preferably, cannula piercing tip 14 makes the incision. In FIG. 10, the anterior capsulorhexis bag is torn by grabbing the anterior capsulorhexis bag flap with the forceps and tearing the bag in a circular orientation. The present invention allows opening and closing of the forceps as well as repositioning of the forceps with the minimal damage to incision the primary incision "α". This feature is accomplished by the coaxial nature of the wire inside the cannula and using only one device as a cystotome for making the secondary incision to the anterior capsulor bag and for use as forceps. Thus, using the same device for the tearing and peeling the flap of the anterior capsulor bag also assists in reducing trauma. The co-axial nature of th(e wire in the cannula is important in reducing trauma to incision "α" when the forceps are opened and closed during re-positioned. Using one device for both functions assists in reducing trauma by eliminating the need to withdraw one instrument and re-enter the eye with another surgical instrument. Lastly, FIG. 11 illustrates the anterior capsulor bag removed.

Figure 13:
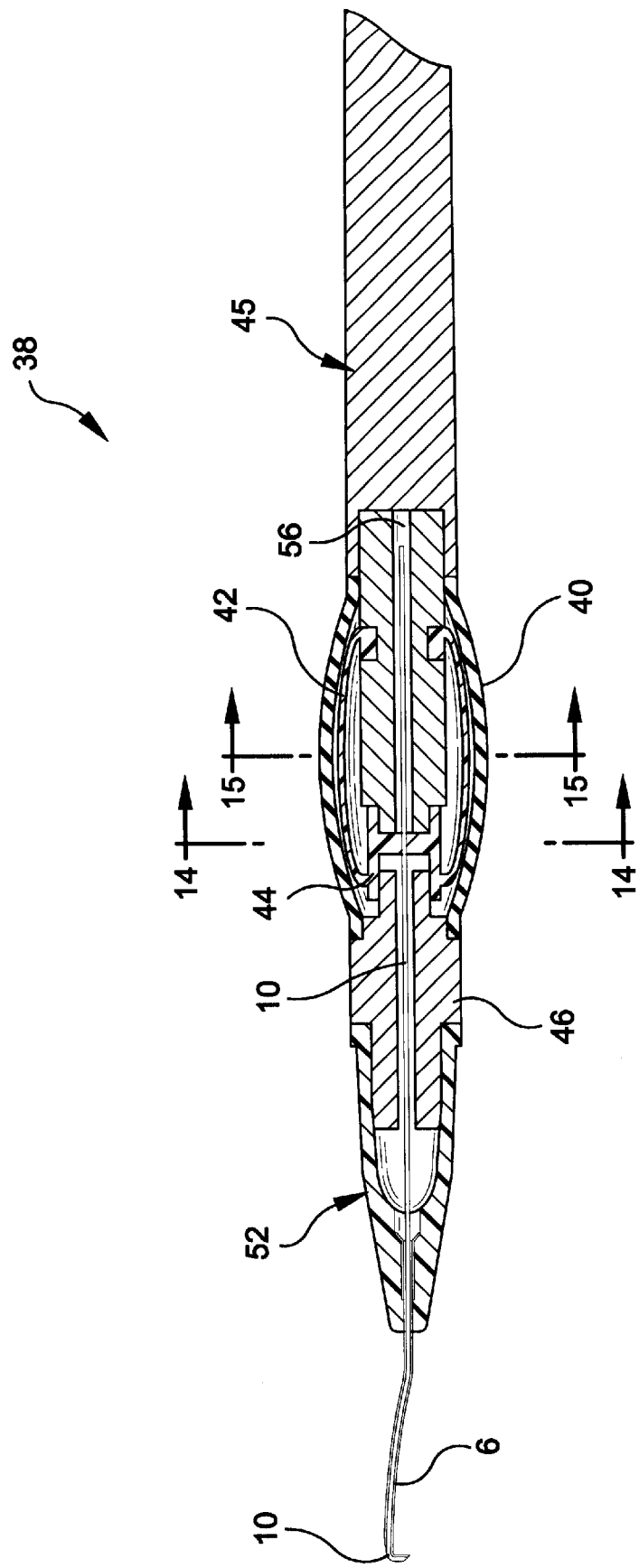
FIG. 13 is a cross-sectional view of FIG. 12 taken along lines 13—13.
Figure 15:
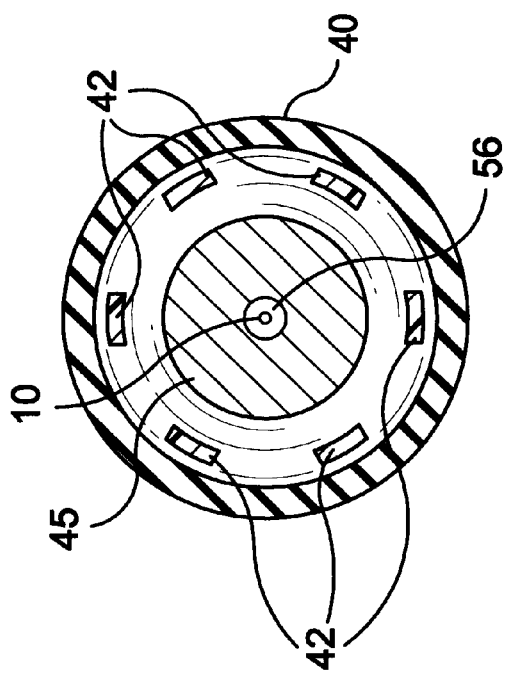
FIG. 15 is a cross-sectional view taken along lines 15—15 in FIG. 13.
Figure 14:
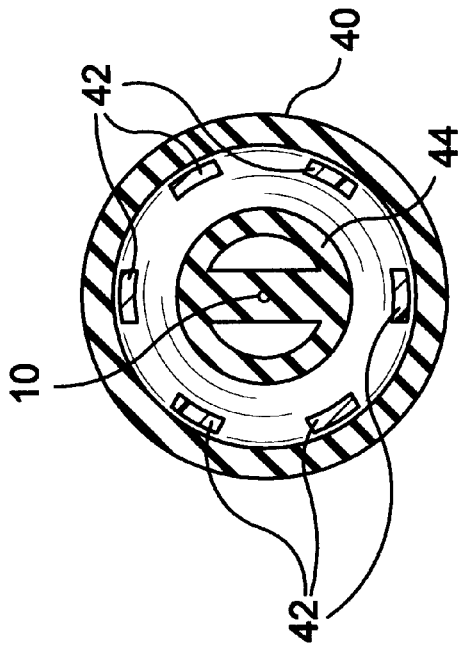
FIG. 14 is a cross-sectional view taken along lines 14—14 in FIG. 13.
Figure 16:
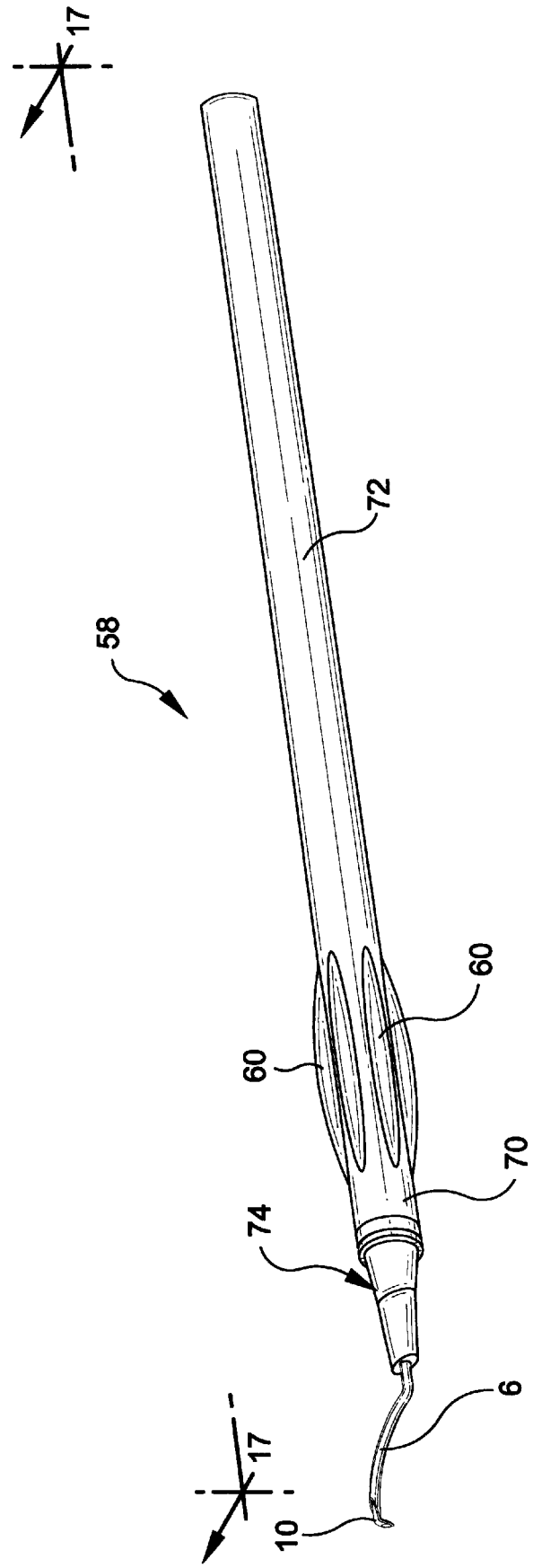
FIG. 16 is another alternative embodiment of the subject invention using multiple bellows.

An alternative embodiment forceps 38 is shown in FIGS. 12–15, wherein the activation grips 40 are totally enclosed. As the preferred embodiment, forceps 38 has wire 10 co-axially disposed in cannula 6. So the advantages of minimal trauma to the "α" incision, replacement of the hub, constant grip on the anterior membrane, and a one-handed technique are preserved. Unlike the invention shown in FIGS. 1–3, opening 8 is totally enclosed. By totally enclosing the activation grips, forceps 38 allows safety and protection to the internal mechanism of the capsulorhexis forceps. Alternatively, to the mechanism shown in FIGS. 1–3, is the mechanisms shown in FIGS. 12–15. Alternative capsulorhexis forceps 38 comprises a leaf spring 42 affixed to diaphragm 40. Leaf spring 42 may have only one spring attached. Preferably, leaf spring 42 may have several of the leaf springs attached to the diaphragm to provide maximum actuation regardless of where the diaphragm is depressed. The diaphragm is made of a resilient material such as thermoplastic elastomers or natural rubber. A handle assembly 45 has a distal end 46 and a proximal end 48. Attached to distal end 46 is a hub assembly 52. Unlike in the preferred embodiment, where the hub assembly had the option to contain a spring, this alternate embodiment preferably does not contain a spring or any resilient member in the hub assembly to move the wire relative to the cannula. FIG. 13 shows that by depressing diaphragm 40 of forceps 38, leaf spring 42 is activated. The leaf spring moves a distal end of leaf spring 44 in the distal direction. The distal end of the leaf spring is slidably attached to the distal end of the handle assembly. In addition, the distal end of the leaf spring is attached to wire 10. Wire 10 moves in a bore 56 inside handle assembly 45. Thus, distal motion of the wire occurs during activation of diaphragm 40. The main advantage of this embodiment is that no spring is required in the hub assembly. Various embodiments can be used as in the last and preferred embodiment by positioning the wire either in the distal or proximal position relative to the cannula as previously described. This feature gives the surgeon the added flexibility of having the forceps either in the open or closed position during the initial operation of the device. Additionally, hub assembly 45 is replaceable giving the added advantage of replacement if damage occurs to the hub assembly. Thus, the same handle assembly can be used and another forceps do not have to be opened and used.

Figure 19:
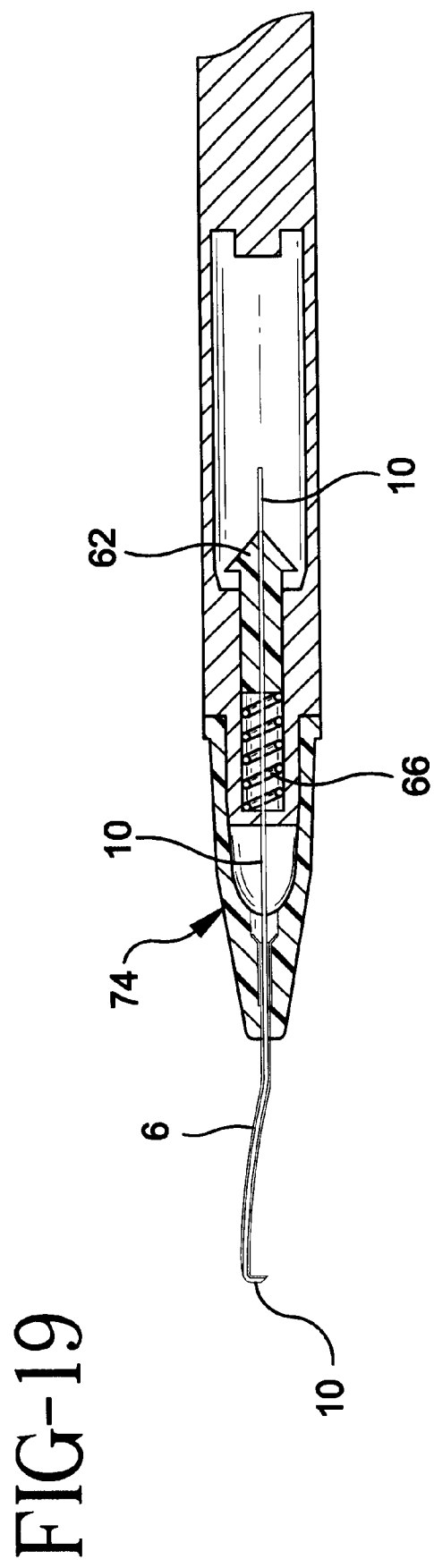
FIG. 19 is a sectional view of FIG. 18 taken along lines 19—19.

Adverting to FIGS. 16–19, shown is another alternative embodiment of the present invention. A forceps 58 include a multiple bellows 60, a piston 62, and a compression spring 66. Like the preferred embodiment, wire 10 is co-axially disposed within cannula 6. As shown in FIGS. 17 and 19, compression spring 66 is attached to piston 62. The spring does not need to be fixedly attached, but merely needs to make contact with the piston. Preferably, piston 62 is removably attached to wire 64. Also included in forceps 58 is a handle 72 and a housing 70. A hub assembly 74 is attached to a distal end 80 of housing 70.

Hub assembly 74 does not include a spring mechanism as optioned in the preferred embodiment. A cavity 76 allows the distal end of the housing to be inserted in hub assembly 74. Further included is wire 6 co-axially disposed within cannula 10. There are various orientations of cannula 6 relative to wire 10 as previously illustrated in the preferred embodiment. Preferably, the wire is in the distal position as shown in FIGS. 17 and 19 to allow the surgeon to have a visual indication of the wire. Activation of the bellows pushes the piston in the distal direction thereby compressing spring 66 and moving the wire in a distal position. As previously described, the forceps can either be in the opened or closed position before activation merely by switching the position of the wire relative to the cannula.

Figure 20:
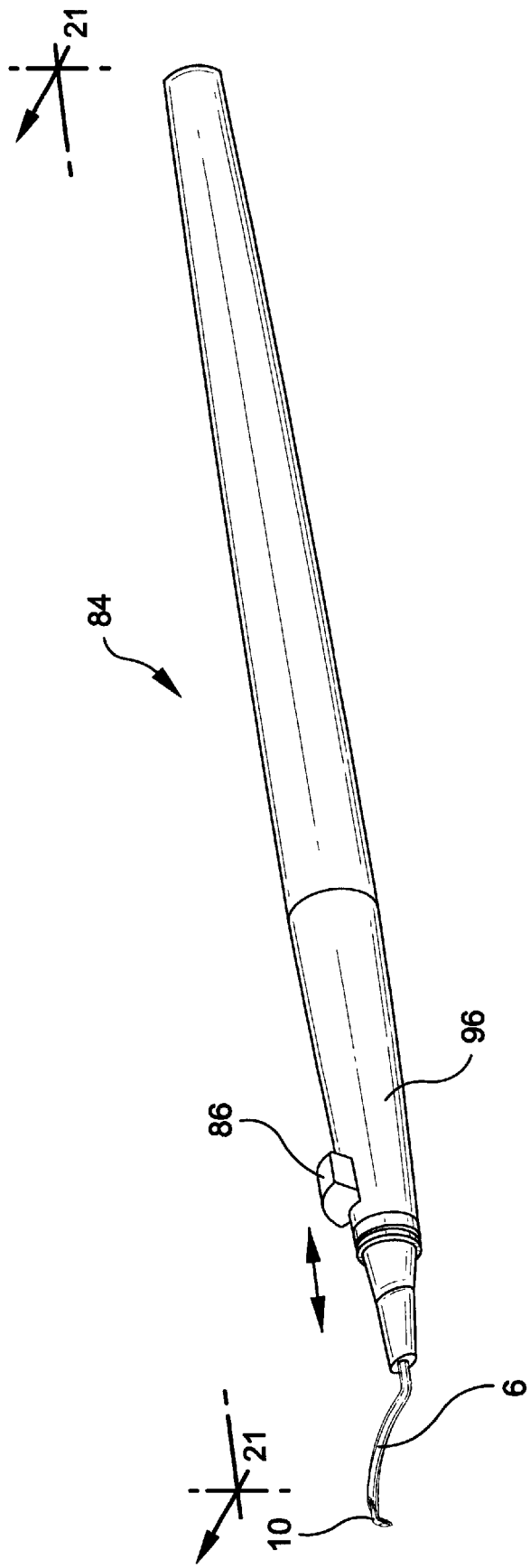
FIG. 20 is an alternate embodiment with an alternative actuation grip.

Another alternate embodiment is shown in FIGS. 20–22. In this embodiment, a forceps 84 is activated by linear motion of a actuation tab 86. This actuation is unlike the other embodiments that where actuated by depressing vertically. However, like the preferred and other alternate embodiments, forceps 84 includes wire 6 co-axially disposed within cannula 10. A hub assembly 92 has a hub 94 attached to cannula 10. A handle 96 is attached to hub assembly 92. However, in this embodiment, linear motion moves the wire to the distal or proximal position instead of vertical motion or compression as in the previous embodiments. An advantage of this embodiment as well as the previous embodiments is that the forceps allows a constant force on the flap thereby eliminating the variable of manual pressure on the forceps. In this alternate embodiment, a spring 90 allows constant force on the anterior membrane. By sliding actuation tab 86, which is attached to wire 10, spring 90 is compressed distally moving wire 10. Open release of tab 86, spring 90 returns wire 10 back to its initial position. Again, this embodiment allows replacement of hub assembly 92. This embodiment also has flexibility in use by offering the wire and cannula in the initially closed or open position by changing the orientation relative to each other as shown in the preferred embodiment.

In summary, by providing the capsulorhexis forceps in the present invention, the forceps allows the hub to be replaced. The forceps also allows constant force on the wire that eliminates the variable of manual pressure on the forceps and variations of pressure that can cause trauma to the flap during re-positioning of the forceps. In addition, the present invention provides flexibility to the surgeon by allowing an initially open or closed position of the forceps by utilizing the same device by merely replacing the hub assembly. In addition, trauma to the primary incision in the scleral tunnel or clear cornea is minimized because the forceps allows incision and peeling all in one device through the co-axial wire disposed in the cannula. Repositioning or opening and closing the forceps that may be required during the tearing or peeling procedure can easily be done without major trauma to the primary incision by providing the forceps with the co-axial wire inside the cannula. Finally, if the wire or cannula is damaged during use, simple replacement is allowed without complete replacement of the entire forceps.

What is claimed is:

1. A capsulorhexis forceps, comprising:
   a hub having a first end and a second end;
   a cannula having a proximal portion, a sharpened distal portion for making incisions, and a lumen therethrough, said proximal portion fixedly attached to said first end; and
   a wire coaxially disposed within said lumen and having a front and a back end, said front end movable relative to said cannula such that the forceps can grip and tear using a constant force without moving said cannula,
   said hub further comprising a spring disposed inside said hub to provide a constant tension on said wire for gripping tissue and a cap attached to said second end of said wire, said spring disposed over said wire and in contact with said cap such that said wire returns to said initial position after movement of said wire.

said distal portion and said front end being bent at approximately 90 degrees from said proximal portion of said cannula and said back end of said wire.

2. The forceps of claim 1, further comprising:

a handle assembly attached to said second end of said hub and said wire, said handle assembly for providing movement of said wire with a constant force independent of manual activation force.

3. The forceps of claim 1, further comprising:

a handle assembly attached to said second end of said hub and said wire, said handle assembly providing movement of said wire dependent of manual activation force.

4. The forceps of claim 2, wherein said wire is initially in a closed position relative to said cannula.

5. The forceps of claim 2, wherein said wire is initially in an open position relative to said cannula.

6. The forceps of claim 2, wherein said hub is removably attached to said handle assembly.

7. The forceps of claim 1, wherein said cannula and said wire are arcuate.

8. The forceps of claim 7, wherein said front end of said wire is distal to said distal end of said cannula.

9. The forceps of claim 7, wherein said front end of said wire is proximal to said distal end of said cannula.

10. The forceps of claim 7, wherein said wire linearly moves relative to said cannula.

11. The forceps of claim 1, wherein said wire moves in a direction proximal to distal relative to said cannula.

12. The forceps of claim 1, wherein said wire moves in a direction distal to proximal relative to said cannula.

13. The forceps of claim 1, wherein said cannula is used as cystotome.

14. A capsulorhexis forceps, comprising:

a removable hub assembly including a hub, a cannula having a proximal portion, a sharpened distal portion and a lumen therethrough, and a wire having a front and a back end, said cannula attached to said hub, said wire coaxially disposed within said lumen such that the forceps can grip and tear without moving said cannula, said sharpened distal portion of said cannula and said front end of said wire being bent at approximately 90 degrees to grip tissue; and a handle assembly attached to said hub assembly for moving said wire, said assembly including a handle at least one activation grip and a wire actuation system attached to said grip such that manual force on said grip moves said wire by said actuation system from an initial position relative to said cannula with a constant force independent of manual force applied on said grip, said removable hub assembly further comprising a spring disposed inside said hub to provide a constant tension on said wire for gripping tissue and a cap attached to said back end of said wire, said sprint disposed over said wire and in contact with said cap such that said wire returns to said initial position after movement of said wire.

15. The forceps of claim 14 wherein said wire actuation system includes a cup attached to said cap, a central shaft attached to said cup and a leaf spring attached to both said central shaft and said grip.

16. The forceps of claim 15, wherein said leaf spring is positioned on said central shaft to move said wire in a direction proximal to distal relative to said cannula.

17. The forceps of claim 15, wherein said leaf spring is positioned on said central shaft to move said wire in a direction distal to proximal relative to said cannula.

18. A method of using a capsulorhexis forceps, comprising:

holding a capsulorhexis forceps of the type having a hub, a cannula with a proximal portion attached to said hub, said cannula having a sharpened distal portion and lumen therethrough, a wire coaxially disposed within said lumen and having a front and a back end, said front end movable relative to said cannula, said sharpened distal portion and said front end being bent approximately 90 degrees so that said forceps can grip and tear without moving said cannula, and a spring to provide a constant tension on said wire for gripping a flap of tissue and returning the wire to an initial position after movement;

making an initial ocular incision in the sclera or clear corneal for creating an entrance into the anterior chamber;

entering said forceps into the anterior portion of the capsulor bag; cutting into the anterior portion of the capsulor bag to create a flap with said forceps; and grasping said flap between said wire and said distal portion of said cannula using the constant tension from said spring on said wire to grip said flap.

19. The method of claim 18 further including the steps of:

tearing the anterior capsule with said forceps; and re-positioning said forceps and re-grasing the flap to continue tearing the anterior capsule.

20. The method of claim 19 further including the steps of:

removing a portion of the anterior capsule and creating direct access to the lens from the anterior chamber.

\* \* \* \* \*